United States Patent
Babkes (10) Patent No.: US 9,233,016 B2
(45) Date of Patent: Jan. 12, 2016

(54) ELEVATING STOMACH STIMULATION DEVICE

(75) Inventor: Mitchell H. Babkes, Santa Clarita, CA (US)

(73) Assignee: APOLLO ENDOSURGERY, INC., Austin, TX (US)

(*) Notice: Subject to any disclaimer, the term of this patent is extended or adjusted under 35 U.S.C. 154(b) by 287 days.

(21) Appl. No.: 13/272,116

(22) Filed: Oct. 12, 2011

(65) Prior Publication Data

US 2012/0095493 A1 Apr. 19, 2012

Related U.S. Application Data

(60) Provisional application No. 61/394,318, filed on Oct. 18, 2010.

(51) Int. Cl.
*A61M 29/00* (2006.01)
*A61F 5/00* (2006.01)

(52) U.S. Cl.
CPC ............... *A61F 5/003* (2013.01); *A61F 5/0036* (2013.01)

(58) Field of Classification Search
CPC ...... A61F 5/0003; A61F 5/003; A61F 5/0036
USPC ......... 606/191, 192, 198; 604/909; 623/23.65
See application file for complete search history.

(56) References Cited

U.S. PATENT DOCUMENTS

| | | |
|---|---|---|
| 4,416,267 A | 11/1983 | Garren et al. |
| 4,607,618 A | 8/1986 | Angelchik |
| 4,648,383 A | 3/1987 | Angelchik |
| 4,739,758 A | 4/1988 | Lai et al. |
| 4,774,956 A | 10/1988 | Kruse et al. |
| 4,844,068 A | 7/1989 | Arata et al. |
| 4,899,747 A | 2/1990 | Garren et al. |
| 4,925,446 A | 5/1990 | Garay et al. |
| 5,084,061 A | 1/1992 | Gau et al. |
| 5,259,399 A | 11/1993 | Brown |
| 5,312,343 A | 5/1994 | Krog et al. |
| 5,820,584 A | 10/1998 | Crabb |
| 6,264,700 B1 | 7/2001 | Kilcoyne et al. |
| 6,322,538 B1 | 11/2001 | Elbert et al. |
| 6,454,785 B2 | 9/2002 | De Hoyos Garza |
| 6,540,789 B1 | 4/2003 | Silverman et al. |

(Continued)

FOREIGN PATENT DOCUMENTS

| | | |
|---|---|---|
| DE | 102007025312 | 11/2008 |
| EP | 1397998 | 3/2004 |

(Continued)

*Primary Examiner* — Richard Louis
(74) *Attorney, Agent, or Firm* — Gordon & Jacobson, P.C.

(57) ABSTRACT

The medical systems, apparatuses and uses thereof for treating obesity and/or obesity-related diseases are provided which relate to devices designed to stimulate an internal surface of the stomach such as the cardia. Features of the obesity treatment devices include insertion of said devices transorally and without invasive surgery, without associated patient risks of invasive surgery, and without substantial patient discomfort. The devices include flotation portions and cardia-stimulating portions, so that as the level of stomach contents rise, the devices will contact and stimulate the nerves in the cardia region of the stomach to induce satiety. The devices may have non-inflatable balls, be made of skinned foam, have ballast members such as a weighted ball or quantity of saline for orientation, and various combinations thereof.

9 Claims, 5 Drawing Sheets

(56) References Cited

U.S. PATENT DOCUMENTS

| | | |
|---|---|---|
| 6,579,301 B1 | 6/2003 | Bales et al. |
| 6,675,809 B2 | 1/2004 | Stack et al. |
| 6,733,512 B2 | 5/2004 | McGhan |
| 6,845,776 B2 | 1/2005 | Stack et al. |
| 6,981,978 B2 | 1/2006 | Gannoe |
| 6,981,980 B2 | 1/2006 | Sampson et al. |
| 6,994,095 B2 | 2/2006 | Burnett |
| 7,008,419 B2 | 3/2006 | Shadduck |
| 7,033,384 B2 | 4/2006 | Gannoe et al. |
| 7,037,344 B2 | 5/2006 | Kagan et al. |
| 7,056,305 B2 | 6/2006 | Garza Alvarez |
| 7,090,699 B2 | 8/2006 | Geitz |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,320,696 B2 | 1/2008 | Gazi et al. |
| 7,347,875 B2 | 3/2008 | Levine et al. |
| 7,354,454 B2 | 4/2008 | Stack et al. |
| 7,476,256 B2 | 1/2009 | Meade et al. |
| 7,510,559 B2 | 3/2009 | Deem et al. |
| 7,608,114 B2 | 10/2009 | Levine et al. |
| 7,682,330 B2 | 3/2010 | Meade et al. |
| 7,695,446 B2 | 4/2010 | Levine et al. |
| 7,699,863 B2 | 4/2010 | Marco et al. |
| 7,753,870 B2 | 7/2010 | Demarais et al. |
| 7,771,382 B2 | 8/2010 | Levine et al. |
| 7,794,447 B2 | 9/2010 | Dann et al. |
| 7,815,589 B2 | 10/2010 | Meade et al. |
| 7,837,643 B2 | 11/2010 | Levine et al. |
| 7,841,503 B2 | 11/2010 | Sonnenschein et al. |
| 7,931,693 B2 | 4/2011 | Binmoeller |
| 7,981,162 B2 | 7/2011 | Stack et al. |
| 8,029,455 B2 | 10/2011 | Stack et al. |
| 8,032,223 B2 | 10/2011 | Imran |
| 2003/0109935 A1 | 6/2003 | Geitz |
| 2003/0153905 A1 | 8/2003 | Edwards et al. |
| 2004/0044357 A1 | 3/2004 | Gannoe et al. |
| 2004/0092892 A1 | 5/2004 | Kagan et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2005/0049718 A1 | 3/2005 | Dann et al. |
| 2005/0055039 A1 | 3/2005 | Burnett et al. |
| 2005/0085923 A1 | 4/2005 | Levine et al. |
| 2005/0096692 A1 | 5/2005 | Linder et al. |
| 2005/0165389 A1* | 7/2005 | Swain et al. ............ 606/27 |
| 2005/0192614 A1 | 9/2005 | Binmoeller |
| 2005/0197714 A1 | 9/2005 | Sayet |
| 2005/0228504 A1* | 10/2005 | Demarais ............ 623/23.65 |
| 2005/0267595 A1* | 12/2005 | Chen et al. ............ 623/23.65 |
| 2005/0267596 A1 | 12/2005 | Chen et al. |
| 2005/0273060 A1 | 12/2005 | Levy et al. |
| 2006/0178691 A1 | 8/2006 | Binmoeller |
| 2006/0252983 A1 | 11/2006 | Lembo et al. |
| 2007/0010864 A1 | 1/2007 | Dann et al. |
| 2007/0016262 A1 | 1/2007 | Gross et al. |
| 2007/0021761 A1 | 1/2007 | Phillips |
| 2007/0078476 A1 | 4/2007 | Hull, Sr. et al. |
| 2007/0083224 A1 | 4/2007 | Hively |
| 2007/0100368 A1 | 5/2007 | Quijano et al. |
| 2007/0118168 A1 | 5/2007 | Lointier et al. |
| 2007/0156013 A1 | 7/2007 | Birk |
| 2007/0173881 A1 | 7/2007 | Birk et al. |
| 2007/0185374 A1 | 8/2007 | Kick et al. |
| 2007/0239284 A1 | 10/2007 | Skerven et al. |
| 2007/0250088 A1* | 10/2007 | Makower et al. ............ 606/157 |
| 2007/0265598 A1 | 11/2007 | Karasik |
| 2007/0293716 A1 | 12/2007 | Baker et al. |
| 2008/0015618 A1 | 1/2008 | Sonnenschein et al. |
| 2008/0058840 A1 | 3/2008 | Albrecht et al. |
| 2008/0058887 A1 | 3/2008 | Griffin et al. |
| 2008/0097513 A1 | 4/2008 | Kaji et al. |
| 2008/0109027 A1* | 5/2008 | Chen et al. ............ 606/191 |
| 2008/0208241 A1 | 8/2008 | Weiner et al. |
| 2008/0221595 A1 | 9/2008 | Surti |
| 2008/0234718 A1 | 9/2008 | Paganon et al. |
| 2008/0234834 A1 | 9/2008 | Meade et al. |
| 2008/0243166 A1 | 10/2008 | Paganon et al. |
| 2008/0249635 A1 | 10/2008 | Weitzner et al. |
| 2008/0255678 A1 | 10/2008 | Cully et al. |
| 2008/0262529 A1 | 10/2008 | Jacques |
| 2009/0012553 A1 | 1/2009 | Swain et al. |
| 2009/0082644 A1* | 3/2009 | Li ................ 600/302 |
| 2009/0093767 A1 | 4/2009 | Kelleher |
| 2009/0149879 A1 | 6/2009 | Dillon |
| 2009/0171382 A1* | 7/2009 | Dillon et al. ............ 606/192 |
| 2009/0198210 A1 | 8/2009 | Burnett et al. |
| 2009/0259246 A1 | 10/2009 | Eskaros et al. |
| 2009/0275973 A1 | 11/2009 | Chen et al. |
| 2009/0287231 A1* | 11/2009 | Brooks et al. ............ 606/155 |
| 2009/0299486 A1 | 12/2009 | Shohat et al. |
| 2009/0312597 A1 | 12/2009 | Bar et al. |
| 2010/0030017 A1 | 2/2010 | Baker et al. |
| 2010/0049224 A1 | 2/2010 | Vargas |
| 2010/0100115 A1 | 4/2010 | Soetermans et al. |
| 2010/0121371 A1 | 5/2010 | Brooks et al. |
| 2010/0168782 A1 | 7/2010 | Hancock |
| 2010/0249822 A1 | 9/2010 | Nihalani |
| 2010/0256775 A1 | 10/2010 | Belhe et al. |
| 2010/0256776 A1 | 10/2010 | Levine et al. |
| 2010/0305590 A1 | 12/2010 | Holmes et al. |
| 2010/0331756 A1 | 12/2010 | Meade et al. |

FOREIGN PATENT DOCUMENTS

| | | |
|---|---|---|
| EP | 1774929 | 4/2007 |
| FR | 2892297 | 4/2007 |
| FR | 2941617 | 8/2010 |
| WO | WO 88/00027 | 1/1988 |
| WO | 0032092 | 6/2000 |
| WO | 2005094257 | 10/2005 |
| WO | WO 2005/097012 | 10/2005 |
| WO | WO 2005/110280 | 11/2005 |
| WO | 2006044640 | 4/2006 |
| WO | WO 2006/111961 | 10/2006 |
| WO | WO 2006/118744 | 11/2006 |
| WO | WO 2007/027812 | 3/2007 |
| WO | WO 2007/053556 | 5/2007 |
| WO | 2007076021 | 7/2007 |
| WO | WO 2007/092390 | 8/2007 |
| WO | WO 2007/110866 | 10/2007 |
| WO | 2008101048 | 8/2008 |
| WO | WO 2008/112894 | 9/2008 |
| WO | WO 2008/132745 | 11/2008 |
| WO | WO 2010/042062 | 4/2010 |
| WO | WO 2010/074712 | 7/2010 |
| WO | WO 2010/087757 | 8/2010 |
| WO | WO 2010/117641 | 10/2010 |

* cited by examiner

ELEVATING STOMACH STIMULATION DEVICE

RELATED APPLICATIONS

The present application claims priority under 35 U.S.C. §119 to U.S. Provisional Application No. 61/394,318, filed on Oct. 18, 2010, the disclosure of which is incorporated by reference herein.

FIELD OF THE INVENTION

The present invention generally relates to medical systems, apparatus and uses thereof for treating obesity and/or obesity-related diseases, and more specifically, relates to devices designed to stimulate an internal surface of the stomach.

BACKGROUND OF THE INVENTION

Over the last 50 years, obesity has been increasing at an alarming rate and is now recognized by leading government health authorities, such as the Centers for Disease Control (CDC) and National Institutes of Health (NIH), as a disease. In the United States alone, obesity affects more than 60 million individuals and is considered the second leading cause of preventable death. Worldwide, approximately 1.6 billion adults are overweight, and it is estimated that obesity affects at least 400 million adults.

Obesity is caused by a wide range of factors including genetics, metabolic disorders, physical and psychological issues, lifestyle, and poor nutrition. Millions of obese and overweight individuals first turn to diet, fitness and medication to lose weight; however, these efforts alone are often not enough to keep weight at a level that is optimal for good health. Surgery is another increasingly viable alternative for those with a Body Mass Index (BMI) of greater than 40. In fact, the number of bariatric surgeries in the United States is projected to reach approximately 400,000 annually by 2010.

Examples of surgical methods and devices used to treat obesity include the The LAP-BAND® (Allergan, Inc., Irvine, Calif.) gastric band and the LAP-BAND AP® (Allergan, Inc., Irvine, Calif.) gastric band. However, surgery might not be an option for every obese individual; for certain patients, non-surgical therapies or minimal-surgery options are more effective or appropriate.

In the early 1980s, physicians began to experiment with the placement of intragastric balloons to reduce the size of the stomach reservoir, and consequently its capacity for food. Once deployed in the stomach, the balloon helps to trigger a sensation of fullness and a decreased feeling of hunger. These devices are designed to provide therapy for moderately obese individuals who need to shed pounds in preparation for surgery, or as part of a dietary or behavioral modification program. These balloons are typically cylindrical or pear-shaped, generally range in size from 200-500 ml or more, are made of an elastomer such as silicone, polyurethane, or latex, and are filled with air, an inert gas, water, or saline.

One such inflatable intragastric balloon is described in U.S. Pat. No. 5,084,061 and is commercially available as the BioEnterics Intragastric Balloon System ("BIB System", sold under the trademark ORBERA). The BIB System comprises a silicone elastomer intragastric balloon that is inserted into the stomach and filled with fluid. Conventionally, the balloons are placed in the stomach in an empty or deflated state and thereafter filled (fully or partially) with a suitable fluid. The balloon occupies space in the stomach, thereby leaving less room available for food and creating a feeling of satiety for the patient. Clinical results with these devices show that for many obese patients, the intragastric balloons significantly help to control appetite and accomplish weight loss.

Placement of such balloons is temporary, and such balloons are typically removed after about six months. One means of removing the balloon is to deflate it by puncturing the balloon, and either aspirating the contents of the balloon or allowing the fluid to pass into the patient's stomach. Alternatively, if the balloon is left in place beyond its designed lifetime, the acids present in a patient's stomach may erode the balloon to the point where it self-deflates. When this occurs, the deflated balloon may pass naturally through the patient's digestive system and be expelled through the bowel. For instance, McGhan, U.S. Pat. No. 6,733,512, describes a self-deflating intragastric balloon that includes a biodegradable inflation valve. After a certain residence time in the stomach, the valve starts to leak and eventually the balloon deflates and passes though the patient's digestive tract.

Despite the advances in the design of intragastric balloons, there remains a need for improved medical systems, apparatus and uses thereof for treating obesity and/or obesity-related diseases, and more specifically, to devices designed to stimulate an internal surface of the stomach such as the cardia.

SUMMARY OF THE INVENTION

The medical systems, apparatus and uses thereof for treating obesity and/or obesity-related diseases described herein relate to devices designed to stimulate an internal surface of the stomach such as the cardia. This pressure or stimulation generally promotes a feeling of satiety reducing the amount of food consumed or digested by the patient. The medical systems, apparatus and uses thereof for treating obesity and/or obesity-related diseases described herein may also relate to reducing the space in the stomach, thus advantageously reducing the amount of food consumed or digested by the patient.

In one embodiment, an implantable device is configured to be placed in a stomach of a patient to elevate with increased stomach contents and stimulate the cardia of the stomach. The device comprises an elastic elongated member that has a three-dimensional relaxed configuration and a generally linear stressed configuration. The relaxed configuration includes a flotation portion commencing at a second end of the elongated member, the flotation portion having a generally two-dimensional shape defining a plane. The relaxed configuration further includes a cardia-stimulating portion terminating at a first end of the elongated member, the cardia-stimulating portion being oriented generally perpendicular to the flotation portion. A plurality of spaced buoyant bodies are affixed to the elongated member at spaced locations along the flotation portion. The buoyant bodies are hollow and sealed with air trapped therein so as to provide buoyancy, and each of the buoyant bodies has a size adapted to fit through the esophagus without collapsing. Further, a stimulating body affixes to the first end of the elongated member, the stimulating body having a size adapted to fit through the esophagus without collapsing. The device may be inserted transorally into the stomach in its stressed configuration and permitted to resume its three-dimensional relaxed configuration in the stomach with the cardia-stimulating portion extending toward the cardia region of the stomach. When implanted the flotation portion floats on the surface of fluid within the stomach while the cardia-stimulating portion projects therefrom toward the cardia and contacts the cardia when the device elevates within the stomach from an increase in the contents therein.

Preferably, the buoyant bodies are hollow and sealed so as to be non-inflatable. The buoyant bodies may be substantially spherical balloons. The device may further comprise a weight located within the buoyant bodies, such as a ball bearing or a quantity of saline. Desirably, a plurality of buoyant bodies are evenly spaced around the flotation portion of the elongated member. In one version, the flotation portion generally forms a ring, and the cardia-stimulating portion extends perpendicularly upward therefrom along a central axis of the ring.

Another implantable device disclosed herein comprises an inflatable body generally in the shape of a prolate spheroid defining a longitudinal axis between end poles and an equatorial plane. The inflatable body has an exterior surface with alternating longitudinal ribs and channels. An internal tube mounts within the inflatable body and extends between the end poles, the internal tube being formed of a material that is stiffer than the material of the inflatable body. Finally, at least one fill valve mounts to one end of the internal tube for injecting air or an inert gas into an inner chamber of the inflatable body. The implantable device is configured for insertion in the stomach with the inflatable body deflated and collapsed around the internal tube, and configured for implant in the stomach with the inflatable body inflated at least partly with air or an inert gas for flotation on the contents of the stomach such that one of the end poles contacts the cardia when the device elevates within the stomach from an increase in the contents therein.

In the preceding device, the fill valve may open into a lumen of the internal tube which has a plurality of through holes distributed along its length for the delivery of air or an inert gas into the internal chamber. There may be two fill valves separately mounted to both ends of the internal tube, and wherein each fill valve opens into a lumen of the internal tube which has a plurality of through holes distributed along its length for the delivery of a fluid into the internal chamber. The longitudinal axis may be oriented in a Z-axis, and each half of the implantable device across the equatorial plane is substantially symmetric along X and Y axes. Desirably, the implantable device is substantially symmetric along the Z axis such that both halves are symmetric to one another. The device may further include a removable belt placed around the equatorial plane to aid in forming the desired shape of the implantable device as the chamber is filled with at least one of air/inert gas or liquid. In one form, the ribs radiate toward the equator from each end pole, and may terminate short of the equator to define the equatorial channel by virtue of the spaces between the ends of the ribs.

Another implantable device that elevates with increased stomach contents to stimulate the cardia of the stomach includes a molded skinned foam member having an elongated central shaft defining a longitudinal axis. The shaft terminates at each end in a dish having a larger radial dimension than the shaft and having a plurality of openings therethrough. A central, weighted stabilizing disk oriented generally in a plane perpendicular to the central shaft has a plurality of axial openings therethrough. Upon implant in the stomach, the device floats on the contents of the stomach such that one of the dishes contacts the cardia when the device elevates within the stomach from an increase in the contents therein. The shaft is preferably tubular and has a plurality of openings therein. The stabilizing disk may have embedded weights such as ball bearings therein for stability. The implantable device is desirably compressible into a transoral insertion configuration. The device is also preferably substantially axisymmetric and symmetric across the stabilizing disk.

A still further floating implantable device disclosed herein for stimulating the cardia of the stomach comprises a foam frame collapsible into a delivery configuration suitable for transoral insertion into the stomach and expandable into an implant configuration having a generally prolate spheroid outer shape oriented about a central axis. The frame includes end poles joined by generally axially-extending struts with circumferential spaces therebetween and surrounding an internal cavity. A plurality of buoyant bodies on the struts are located in a plane perpendicular to the central axis, wherein upon implant in the stomach the device floats on the contents of the stomach such that one of the end poles contacts the cardia when the device elevates within the stomach from an increase in the contents therein. The implantable device further may include a weighted body coupled to one pole of the frame to orient the implantable device in a pre-selected floating position. The weighted body may be a steel cylinder encased in the foam of the frame. There are preferably at least five equal struts arrayed at equal spacing around the central axis and extending between the end poles of the frame. In one embodiment, the struts comprise strips that are radially thin and relatively wide in the circumferential direction. The plurality of buoyant bodies may be located in a plane perpendicular to the central axis about ⅔ down from one pole of the device. Further, the buoyant bodies may comprise wedge-shaped members each having a narrow end pointing toward the central axis and within the internal cavity of the frame, and a wide end outside the internal cavity.

In an alternative embodiment, an implantable device configured to be placed in a stomach of a patient to stimulate the cardia of the stomach includes a semi-flexible member having a first end and a second end, a surface feature coupled to the first end, and a first buoyant body positioned along a portion of the semi-flexible member. The surface feature may be configured to stimulate the cardia.

The implantable device may be configurable in a substantially elongated first position for insertion in the stomach. In some embodiments, the implantable device may be configured to be inserted into a cylinder while in the first position for insertion into the stomach. The implantable device may be configurable in a second position for floating on the surface of the contents of the stomach to facilitate stimulating the cardia. The second end and a portion of the semi-flexible member may form a portion of a circle when the implantable device is in the second position. The implantable device may be configured to automatically change from the first position to the second position upon insertion in the stomach.

In one embodiment, the buoyant body may be positioned along the semi-flexible member to aid the implantable device in floating on the surface of the contents of the stomach. The implantable device may include a second buoyant body coupled to the surface feature. The first buoyant body may be a substantially smooth, substantially spherical balloon. A weight may be located within the first buoyant body. The weight is at least one of a ball bearing or saline.

In some embodiments, the surface feature configured to stimulate the cardia may be oriented so that, as the surface of the contents of the stomach rises with sustenance intake, the cardia is stimulated. A plurality of buoyant bodies may be positioned along the semi-flexible member with portions of the semi-flexible member separating the buoyant bodies. The distance the surface feature configured to stimulate the cardia is from the cardia is based on a pre-selected volume of sustenance intake by the patient. The implantable device and/or components of the implantable device may be too large to pass through an opening of the pylorus of the patient.

In an embodiment, an implantable device configured to be placed in a stomach of a patient to treat obesity by stimulating the cardia of the patient is disclosed. The device may include a ribbed buoyant body having an internal chamber, an external surface of the ribbed buoyant body for stimulating the cardia, and a substantially rigid member internal to the ribbed buoyant body for shaping the ribbed buoyant body.

In some embodiments the internal chamber may be configured to be filled with a fluid. The implantable device may be substantially compressed in a first position for insertion in the stomach. The implantable device is substantially non-compressed in a second position for floating on the contents of the stomach. In some embodiments, a greater portion of the implantable device in the second position is above the surface of the contents of the stomach than the portion of the implantable device that is below the surface of the contents of the stomach.

In one embodiment, the substantially rigid member includes a cannula coupled to a one-way valve for the delivery of a fluid into the internal chamber. The cannula may also be coupled to a plurality of delivery conduits coupled to the interior of the chamber. The implantable device may be substantially symmetric in at least one of the X, Y, or Z axes.

In some embodiments the implantable device has a substantially prolate shape once the internal chamber is filled with at least one of air/inert gas or liquid. A removable belt may aid in forming the desired shape of the implantable device as the chamber is filled with at least one of air/inert gas or liquid.

In one embodiment, the external surface of the ribbed buoyant body for stimulating the cardia may be configured to contact the cardia based upon a pre-selected volume of sustenance consumed by the patient. The external surface of the ribbed buoyant body may include channels to allow the passage of ingested sustenance around the implantable device. The surface feature configured to stimulate the cardia may be configured to contact the cardia prior to the level of ingested sustenance and stomach acid contacting and/or applying pressure to the cardia.

In one embodiment, an implantable device configured to be placed in a stomach of a patient to stimulate the cardia of the stomach includes a molded foam member comprising a first end and a second end, a surface feature coupled to the first end to facilitate stimulating the cardia, and a weighted buoyant ring body positioned along a portion of the molded foam member. The weighted buoyant ring may include through holes to facilitate the passage of sustenance through the stomach.

In some embodiments, the implantable device may be substantially compressed in a first position for insertion in the stomach. The implantable device may be substantially non-compressed in a second position for floating on the contents of the stomach. The implantable device may be substantially symmetric in at least one of the X, Y, or Z axes. A concave dish may be coupled to at least one of the first end or the second end of the molded foam member. The concave dish may include through holes to facilitate the passage of sustenance through the stomach.

In an embodiment, the molded foam member may include through holes to facilitate the passage of sustenance through the stomach. The molded foam member may be made from closed cell foam.

In one embodiment, an implantable device configured to be placed in a stomach of the patient to stimulate the cardia of the stomach may include a molded foam member comprising a substantially prolate frame, an opening disposed in the prolate frame to permit the passage of sustenance through the stomach, a surface feature coupled to the prolate frame, a buoyant wedge coupled to the prolate frame to aid the device in floating on the surface of the contents of the stomach, and a weighted body coupled to the prolate frame to orient the implantable device in a pre-selected floating position. The surface feature may be configured to stimulate the cardia.

In some embodiments the implantable device may be substantially compressed in a first position for insertion in the stomach. The implantable device may be substantially non-compressed in a second position for floating on the contents of the stomach. A greater portion of the implantable device may be above the surface of the contents of the stomach than a portion of the implantable device that is below the surface of the contents of the stomach.

DETAILED DESCRIPTION

Persons skilled in the art will readily appreciate that various aspects of the disclosure may be realized by any number of methods and devices configured to perform the intended functions. Stated differently, other methods and devices may be incorporated herein to perform the intended functions. It should also be noted that the drawing figures referred to herein are not all drawn to scale, but may be exaggerated to illustrate various aspects of the invention, and in that regard, the drawing figures should not be construed as limiting. Finally, although the present disclosure may be described in connection with various medical principles and beliefs, the present disclosure should not be bound by theory.

By way of example, the present disclosure will reference certain implantable obesity treatment devices. Nevertheless, persons skilled in the art will readily appreciate that the present disclosure advantageously may be applied to one of the numerous varieties of implantable obesity treatment devices.

In one embodiment, these implantable obesity treatment devices described herein are intended to be placed inside the patient, without invasive surgery, without associated patient risks of invasive surgery and without substantial patient discomfort. Recovery time may be minimal as extensive tissue healing is generally not required. The life span of these obesity treatment devices may be material-dependent upon long-term survivability within an acidic stomach, but is intended to last one year or longer in various embodiments. Moreover, each device described herein is designed to stimulate an internal surface of the stomach such as the cardia. This pressure or stimulation generally promotes a feeling of satiety reducing the amount of food consumed or digested by the patient. The medical systems, apparatus and uses thereof for treating obesity and/or obesity-related diseases described herein may also relate to reducing the space in the stomach, thus advantageously reducing the amount of food consumed or digested by the patient.

Figures 1A, 1B:
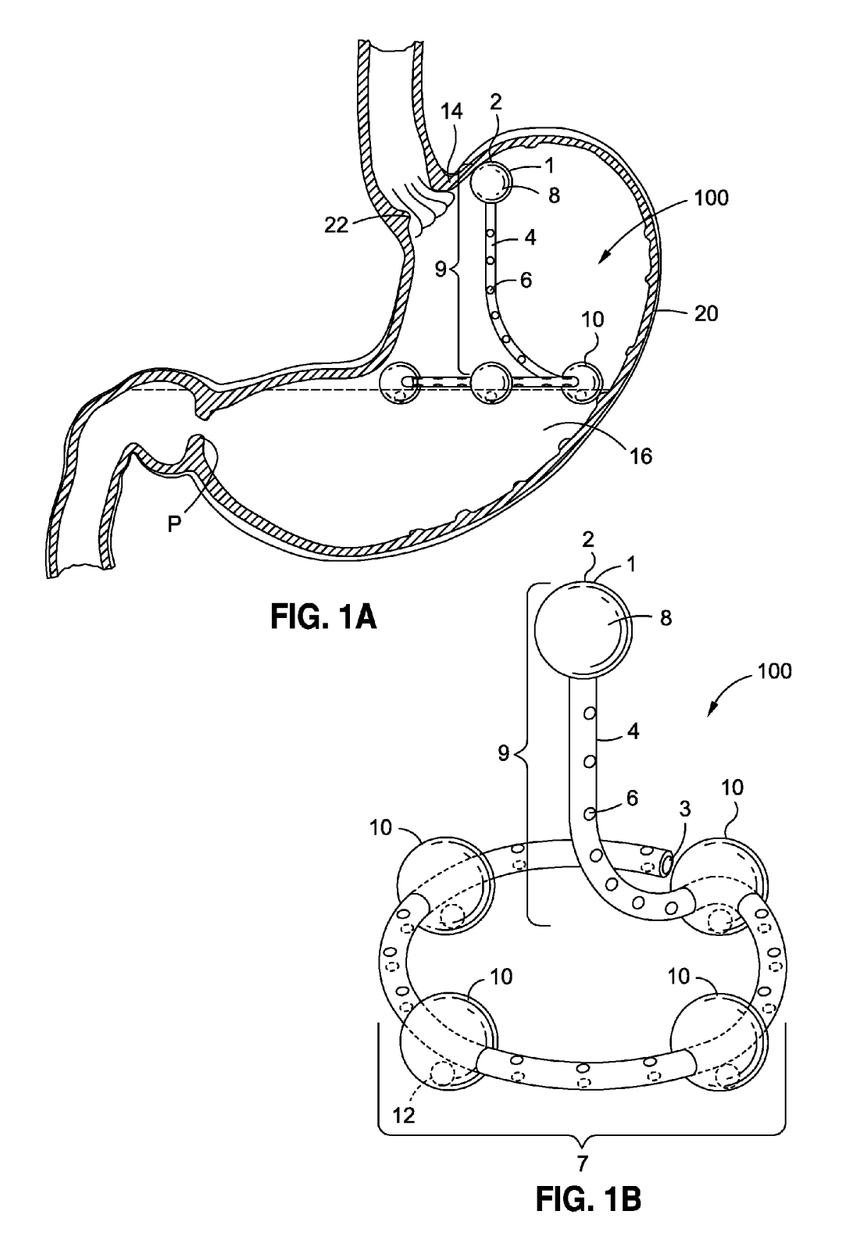
FIG. 1A illustrates a side view of an elevating implantable cardia stimulation device post implantation in the stomach of a patient in accordance with an embodiment of the present invention.
FIG. 1B illustrates a perspective view of the implantable cardia stimulation device of FIG. 1A in accordance with an embodiment of the present invention.

Referring to FIG. 1A, an embodiment of an elevating implantable obesity treatment device 100 is depicted. The implantable obesity treatment device 100 may include an elastic, elongated member 4, a first stimulation end 1 having a stimulation surface 2, a second end 3 and one or more buoyant bodies 10. The first stimulation end 1 terminates in a cardia-stimulating body 8, which may also be buoyant. The stimulating body 8 of the first stimulation end 1 may be any suitable size. For instance, the stimulating body 8 of the first stimulation end 1 may be smaller than, the same size or larger than the one or more buoyant bodies 10 coupled to the elongated member 4. The stimulation surface 2 is preferably rounded or blunt, and may be defined by the exterior of the stimulating body 8, which is desirably spherical.

The buoyant bodies 10 are configured to aid in flotation of the implantable obesity treatment device 100 on or near the surface of the contents of the stomach 16. The contents of the stomach 16 may include stomach acids, partially digested food, consumed food and liquids, sustenance, or the like. Desirably, the elongated member 4 comprises a semi-rigid tube.

The elongated member 4 has a three-dimensional relaxed configuration shown in the figures, and a generally linear stressed configuration (not shown). The relaxed configuration includes a flotation portion 7 commencing at the second end 3 of the elongated member, the flotation portion having a generally two-dimensional shape defining a plane. The relaxed configuration further including a cardia-stimulating portion 9 terminating at the first end 1 of the elongated member, the cardia-stimulating portion 9 being oriented generally perpendicular to the flotation portion 7. In the illustrated embodiment, the flotation portion 7 preferably forms a ring with the cardia-stimulating portion 9 extending perpendicularly upward therefrom along a central axis of the ring.

In use, the implantable obesity treatment device 100 may be inserted transorally into the stomach in its stressed configuration and permitted to resume its three-dimensional relaxed configuration in the stomach with the cardia-stimulating portion 9 extending toward the cardia region of the stomach. The flotation portion 7 floats on the surface of fluid within the stomach while the cardia-stimulating portion 9 projects therefrom toward the cardia. Eventually, after food is ingested, the stimulating body 8 contacts the cardia when the device 100 elevates within the stomach from an increase in the contents therein, at least when the person's torso is upright. Because the cardia-stimulating portion 9 contacts the cardia well before the stomach contents rise to that level, the device 100 stimulates the nerves in the cardia area well before what would occur in the absence of the device, thus contributing to a feeling of satiety well before the person is actually full.

The elongated member 4 may be tubular and comprise one or more through holes 6 configured to permit the passage of the contents of the stomach 16. These through holes 6 may be any suitable size, such as configured to permit the passage of solids or liquids in the stomach 20. Additionally, these through holes 6 may pass through the elongated member 4 at any suitable angle such as horizontal.

The body of the elongated member 4 may be constructed out of polypropylene or other suitable materials configured to resist the acidity of the stomach 20 environment. The material is desirably formed of an elastic material configured to possess "spring-like" memory retention such that elongated member 4 or other components of obesity treatment device 100 exerts a pressure on the stomach 20 walls at various levels within the stomach 20. The elongated member 4 is desirably soft enough to straighten out and fit through the esophagus in a delivery configuration, yet hard enough to resume its as-molded shape and provide spring action upward. Advantageously, the pressure against the stomach 20 walls may trigger the gastric nerves to signal the brain to release hormones that induce the patient to feel full or satiated. In some embodiments, the size of the substantially ring shaped flotation portion 7 may be based on and substantially mirror the interior surface of the stomach 20 at the top level of the contents of the stomach 16. The substantially ring shaped flotation portion 7 may be smaller than the interior surface area of the stomach 20 at the top level of the contents of the stomach 16.

The one or more buoyant bodies 10 may be generally round in shape. For example, the one or more buoyant bodies 10 may be air/inert gas filled, thin walled balloons. In another embodiment, the one or more buoyant bodies 10 may be thin walled balloons filled with air/inert gas and/or a weighted material 12. For instance, the weighted material 12 may comprise any suitable material such as a ball bearing or inert saline. In one embodiment, the ball bearing is approximately a 20 mm metallic ball bearing. In another embodiment, the buoyant bodies 10 are partially filled with saline, such as filled ¼ full of saline, and the rest filled with air or an inert gas. These weighted materials 12 may be added to the buoyant bodies 10 prior to insertion of the implantable obesity treatment device 100 in the stomach 20 of the patient for convenience, or post implantation of the obesity treatment device 100 through any suitable means, such as saline through a one-way valve into under-filled bodies 10.

The weighted material 12 and/or placement of the buoyant bodies 10 may be positioned to support the floating of the device 100 on or near the surface of the contents of the stomach 16 in an orientation where the stimulation surface 2 will make contact with a portion of the stomach 20, such as the cardia 14, upon sustenance intake. For example, four buoyant bodies 10 may be integral to and spaced at fixed regular intervals, such as equal distances along the tube 4. In another embodiment, the buoyant bodies 10 may be integral to and spaced at fixed irregular intervals along the tube 4.

The buoyant bodies 10 may be constructed out of silicon, polypropylene or other suitable materials configured to resist the acidity of the stomach environment. In some embodiments, portions of the implantable obesity treatment device 100, such as the buoyant bodies 10, may comprise surface features, such as channels or ribs to permit the passage of sustenance between a portion of the stomach 20 and the buoyant bodies 10.

In a preferred embodiment, the buoyant bodies 10 are sized to fit through the esophagus without collapsing. That is, the bodies 10 are small enough so that they may be passed through the esophagus, such as through a delivery tube, without collapsing and then having to expand them post-implant. In one embodiment described above, saline may be injected post-implant into each of the bodies 10 for ballast, but the size of the bodies after injection of the saline is desirably still small enough to be extracted through the esophagus without having to collapse them. This greatly simplifies the implant and extraction processes.

As shown in FIG. 1A, in accordance with an embodiment, a flotation portion 7 of the elongated member 4, may be formed in a shape configured to float on or near the surface of the contents of the stomach 16, such as formed in a partial ring or substantially circular shape. For instance, the flotation portion 7 of the implantable obesity treatment device 100 may span from the second end 3 to approximately a midportion of the elongated member 4. The second end 3 may be substantially proximate another portion of the implantable obesity treatment device 100 such that the second end 3 cannot enter or pass through the pylorus. More generally, the flotation portion 7 defines a shape too large to pass through the pylorus. In one particular embodiment, the entire length of the obesity treatment device 100 is at least 30 cm, with the flotation portion 7 formed from approximately 20 cm of the total, and the cardia-stimulating portion 9 projecting upward approximately 10 cm. In this specific embodiment, the ring formed by the flotation portion 7 has a diameter of between 6-7 cm, too large to pass through the pylorus.

The cardia-stimulating portion 9 of the elongated member 4 proximate the first stimulation end 1 may be angled towards the cardia 14 up from the plane created by the substantially ring shaped flotation portion 7 of the implantable obesity treatment device 100. For instance, though the angle may be any suitable angle, in one embodiment, the angle may be normal to the plane created by the substantially ring shaped flotation portion 7 of the implantable obesity treatment device 100. As shown, the cardia-stimulating portion 9 may comprise a section which bends gradually from the plane created by the substantially ring shaped flotation portion 7 and then comprise a substantially non-bending section normal to the plane created by the substantially ring shaped flotation portion 7.

The implantable obesity treatment device 100 may be fabricated in preset sizes, such as small, medium, large, and extra large, or portions of implantable obesity treatment device 100 may be adjustable to facilitate varied stomach volumes and sizes. For example, the cardia-stimulating portion 9 may be made smaller or larger by adding removable section or combinable links (not shown) to increase or decrease the length of the cardia-stimulating portion 9. In other embodiments, the length of the flotation portion 7 may be made larger or smaller by removing or adding links to the second end 3.

In an embodiment, the implantable obesity treatment device 100 may be pre-bent so that it has a substantially ring shaped flotation portion 7 and an angled cardia-stimulating portion 9 as shown in FIG. 1. The implantable obesity treatment device 100 may be deformed into an elongated position for insertion into the stomach 20 of the patient. This elongated or straightened implantable obesity treatment device 100 may be inserted into a suitable implantation device, such as a hollow cylinder or Teflon tube, which will restrict at least the flotation portion 7 of the implantable obesity treatment device 100 from returning to its preferred partial ring shape. The hollow cylinder may be inserted into the mouth of the patient and fed down the esophagus towards the stomach 20. Using tools, such as an endoscope or surgical grabber, the implantable obesity treatment device 100 may be delivered from the hollow cylinder through the lower esophageal sphincter 22 into the stomach 20 of the patient. The components of the implantable obesity treatment device 100 may be sized such that once inserted into the stomach 20 they may not exit through the pylorus P or back through the lower esophageal sphincter 22 until removal is desired. In some embodiments, the implantable obesity treatment device 100 may be delivered through the esophagus to the stomach without the use of the hollow cylinder.

The implantable obesity treatment device 100 may be removed by any suitable means. For instance, the implantable obesity treatment device 100 may be accessed by a surgical grabber and pulled into an elongated shape for removal back up through the hollow cylinder during a medical procedure. The buoyant bodies 10 may be optionally punctured during this procedure or the implantable obesity treatment device 100 may be subdivided into smaller portions using a cutting tool for removal. By adding a radio-opaque additive into a portion of the implantable obesity treatment device 100, such as into the stimulation surface 2, a portion of the implantable obesity treatment device 100 may be seen by an x-ray machine. This additive may aid during the removal process.

In some embodiments, the implantable obesity treatment device 100 may be configured to have digestible valves or segmenting elements to allow the segmented device to pass through the digestive track and bowels of the patient after a predetermined amount of time, such as greater than one year or longer after implantation.

FIG. 1B illustrates a perspective view of the implantable cardia stimulation device 100 according to an embodiment of the present invention. As shown, the first stimulation end 1, having the stimulation surface 2, may be substantially round in shape. This rounded stimulation surface 2 may be configured to stimulate an interior portion of the stomach 20, such as the cardia 14.

Post implantation in the stomach 20, the obesity treatment device 100 may float on or near the surface of the contents 16 of the stomach 20. As additional sustenance is introduced into the stomach, the level of the surface of the contents 16 of the stomach 20 rises. As the level of the surface of the contents 16 of the stomach 20 rises, the stimulation surface 2 nears an interior surface of the stomach 20, such as the cardia 14, and applies a pressure. This pressure stimulates the release of satiety-inducing hormones, thus signaling the patient to slow or stop eating sooner than the patient would without the use of the implantable obesity treatment device 100. Over time, this reduction in intake of sustenance contributes to weight loss of the patient.

The top level of the contents 16 of the stomach 20 is known to change from the horizontal plane with motion of the patient. The orientation and components of the implantable obesity treatment device 100 are configured to be angled accordingly so that the surface angle of the contents 16 of the stomach 20 does not substantially affect the stimulation of a portion of the stomach 20, such as the cardia 14.

Once the device 100 is inserted inside the patient's stomach, appetite suppression may be achieved. In one embodiment, the device 100 may be configured to continuously remain in the patient's stomach 20 for one year or longer, or be able to withstand the stomach's 20 acidic environment.

The device 100 may decrease the stomach's 20 effective volume and capacity. In one embodiment, since there is less room for food, appetite is suppressed, thus reducing calorie consumption. As noted above, the device 100 may be easily implanted inside the patient transorally, without invasive surgery (and the corresponding patient risks inherent in a surgery) and with a minimal recovery time since no extensive tissue healing is required.

Figure 2A:
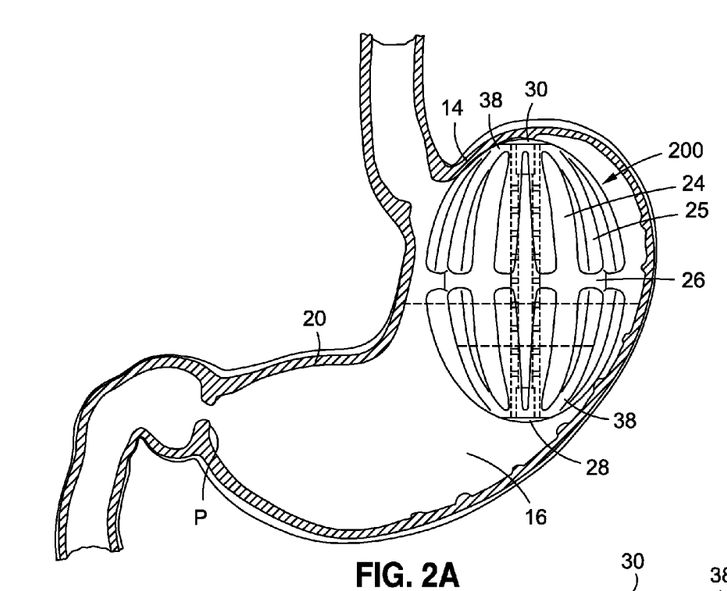
FIG. 2A illustrates a side view of another elevating implantable cardia stimulation device having a fillable internal chamber post implantation in accordance with an embodiment of the present invention.

In a second embodiment of an elevating obesity treatment device as seen in FIG. 2A, an implantable cardia stimulation device 200 formed by an elongated inflatable body 23 defining within a fillable internal chamber 36 is configured to float at or near the surface of the contents 16 of the stomach 20. In one embodiment, the exterior of the device 200 defines one or more longitudinal slots or channels 24 between one or more longitudinal ribs 25 on the exterior surface of the body 23. These channels 24 may be suitably wide to allow the passage of sustenance between the exterior of the device 200 and an interior portion of the stomach 20. The ribs 25 are preferably suitably tall (in radial dimension) to allow proper relief from the interior wall of the stomach 20 to facilitate the passage of sustenance between the exterior of the device and an interior wall of the stomach 20. In one embodiment, the channels 24 have the width of between 1-3 cm, while the ribs 25 project outward from the channels to a distance of between 1-3 cm.

Figure 2B:
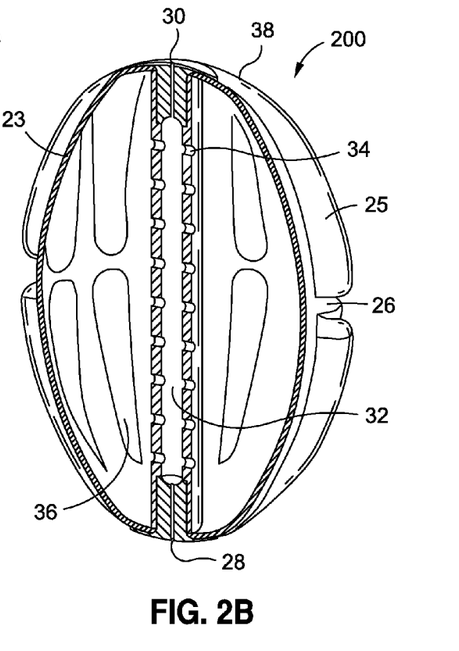
FIG. 2B illustrates a side cutaway view of the implantable cardia stimulation device having a fillable internal chamber, as illustrated in FIG. 2A, in accordance with an embodiment of the present invention.

With reference to FIG. 2B, in some embodiments, the device 200 further comprises an interior substantially rigid tube 32 (or cannula) configured to provide structural support to the inflatable body 23, or aid in the delivery of a fluid such as air/an inert gas or liquid such as saline to the interior chamber 36. The internal tube 32 is formed of a material that is stiffer than the material of the inflatable body 23. For instance, the internal tube 32 may facilitate the forming of the substantially prolate shape of the device 200 (described in greater detail below). The internal tube 32 is coupled axially between the end poles and to the top interior surface and the bottom interior surface of the device 200. The internal tube 32 may comprise through holes 34 configured to deliver air/an inert gas or saline introduced to the tube 32 to the interior chamber 36. The air/an inert gas or saline may be introduced to the internal tube 32 through respective one-way valves 28, 30. These one-way valves 28, 30 may be located on any exterior surface of the device 200, however, in one embodiment, a one-way valve 28, 30 may be coupled to either end of the internal tube 32 and to the top or bottom surface of the device 200. In an alternative embodiment, a single one-way valve may be provided in only one of the end poles of the device 200, which is used for injecting both air/an inert gas and saline.

A filling tube, such as a catheter, may be inserted into each respective one-way valve 28, 30 to facilitate the filling of the internal chamber 36 with air/inert gas or saline. Though any volume of air/inert gas or saline may be added to the internal chamber 36, in one embodiment, the chamber 36 is filled with a combination of ¼ saline and ¾ air/inert gas. The saline acts as a weight to orient the device 200 in the preferred position as shown. In an embodiment where a single one-way valve is used to deliver air/inert gas and saline to the chamber 36, the fill tubes are connected sequentially.

In the illustrated embodiment, the device 200 has an overall prolate spheroid shape, with oval cross-sections oriented about a major central axis between end poles and defining a maximum diameter equator midway along the central axis. A prolate spheroid is a spheroid in which the polar axis is greater than the equatorial diameter. Other rounded and elongated configurations are contemplated, such as a more pointed football or lenticular shape, or a flatter more spherical shape. However, the long axis of the device 200 is desirably at least 50% greater in dimension than the diameter across the equatorial plane, and preferably at least twice as large. In a preferred embodiment, the device 200 is substantially symmetrical in the X, Y and/or Z axis. Thus, should the device 200 rotate or become inverted, the device 200 will function as intended. Stated another way, both the top and the bottom surfaces of the device 200 are configured to stimulate an interior portion of the stomach 20, such as the cardia 14. Alternatively, the shape of the device may be substantially like an egg, which has two halves that are differently shaped from each other but substantially symmetrical about their respective X and Y axes. More accurately, an egg has a shape that has half each a prolate and a roughly spherical (potentially oblate) ellipsoid joined at the equator. An asymmetric shape such as an egg shape may be used with ballast and/or flotation to ensure that one end or the other tends to point upward toward the cardia. For the purpose of definition, all of these shape variations are included in the term "generally prolate spheroid."

Similar to the device 100, the device 200 may be inserted into a suitable implantation device, such as a hollow cylinder or Teflon tube, with the inflatable body 23 in at least a partially deflated state, or having an unfilled status, coupled to two catheters in each one-way valve 28, 30. The hollow cylinder may be inserted into the mouth of the patient and fed down the esophagus towards the stomach 20. Using tools, such as an endoscope or surgical grabber, the device 200 may be delivered from the hollow cylinder through the lower esophageal sphincter 22 into the stomach 20 of the patient. Air/inert gas or saline is then introduced through the respective catheters through the respective one-way valves 28, 30 into the internal tube 32 and into the chamber 36. As air/inert gas or saline is added to the chamber 36, the exterior of the device 200 expands into a prolate spheroid shape. Once inserted into the stomach 20 and filled with air/inert gas or saline, the device 200 may not exit through the pylorus P or back through the lower esophageal sphincter 22 until removal is desired.

In some embodiments, a channel 26 may circumnavigate an exterior portion of the device 200, such as at the midpoint of the device 200. A removable belt (not shown) may be coupled to the channel 26 such as by being tacked or glued into place to aid the device 200 in forming a prolate shape. This belt may be removed at the time of implantation.

Figure 2C:
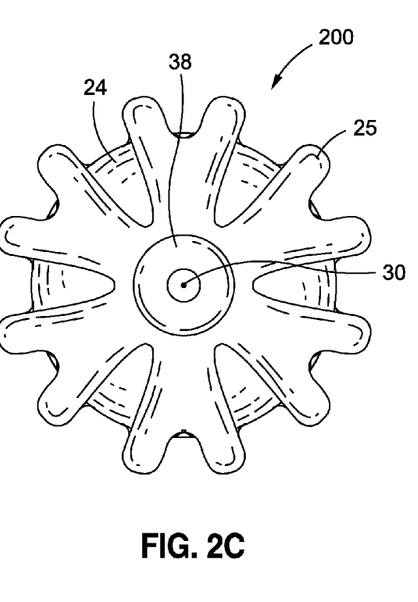
FIG. 2C illustrates a top view of the implantable cardia stimulation device having a fillable internal chamber, as illustrated in FIGS. 2A and 2B, in accordance with an embodiment of the present invention.

FIG. 2C depicts the top view of the device 200 in accordance with an embodiment of the present invention. The channels 24 and the ribs 25 may be any suitable dimension to facilitate the passage of substances (e.g., ingested food) around the cardia stimulation device 200. In one embodiment, the top exterior surface or bottom exterior surface of the device 200, including respective valve 28 and valve 30, comprises a stimulation surface 38. In the illustrated embodiment, the ribs 25 radiate toward the equator from each end pole, and terminate short of the equator to define the equatorial channel 26 by virtue of the spaces between the ends of the ribs. Further, the ribs 25 emanate in pairs which are initially joined and bifurcate a short distance away from the end poles. Additionally, the radial height of each rib 25 increases the farther from the end pole and nearer the equator.

Figure 2D:
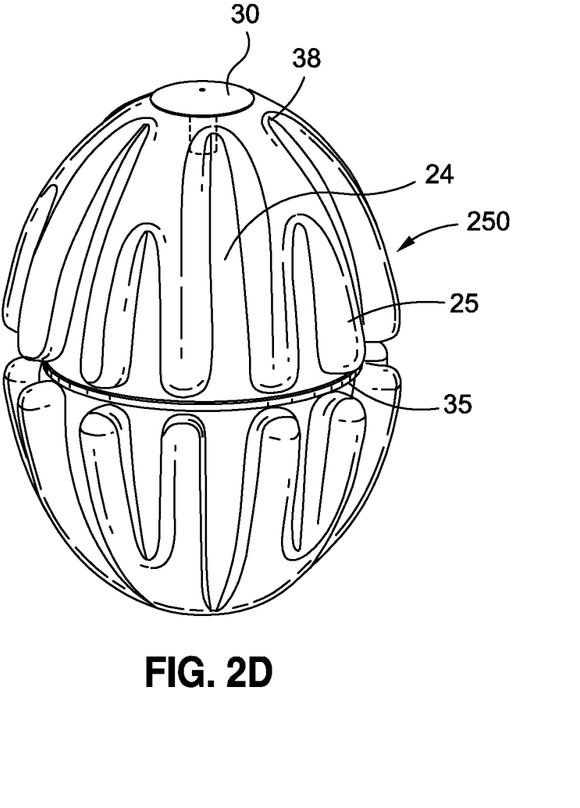
FIG. 2D illustrates an additional embodiment of an implantable cardia stimulation device having an internal chamber in accordance with an embodiment of the present invention.

In another embodiment, as depicted in FIG. 2D, a semi-permanent belt 35 may be coupled to a portion of an implantable cardia stimulation device 250 with a fillable internal chamber 36. The belt 35 may be integral to the exterior of the device 250. In another embodiment, the belt 35 may be coupled to the exterior of the device 250, such as to the channel 26 through any suitable coupling means. The device 250 may optionally comprise an interior chamber 36 without an interior substantially rigid tube 32. Coupled to interior chamber 36 is at least one one-way valve 30 to facilitate the filling of the internal chamber 36 with air/inert gas or saline. In an embodiment, the chamber 36 is filled prior to insertion in the stomach 20 with at least one of fluid or a weighted material. A filling tube, such as a catheter, may be inserted into the one-way valve 30. Similar to device 200, device 250 may comprise channels 24 between one or more ribs 25 on the exterior surface of the device 250.

Figure 3A:
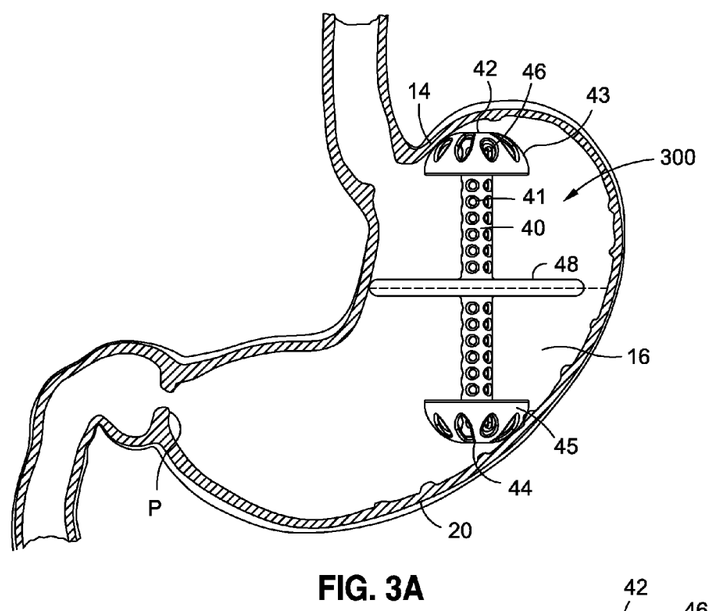
FIG. 3A illustrates a side view of a further elevating implantable foam cardia stimulation device post implantation in the stomach in accordance with an embodiment of the present invention.

FIG. 3A illustrates one embodiment of a side view of an implantable cardia stimulation device 300, post implantation in the stomach 20 of a patient. The device 300 comprises an elongated central shaft 40 defining a longitudinal axis and having a first end 42 and a second end 44. In some embodiments, the shaft 40 is desirably tubular and hollow and comprises a plurality of through holes 41 that are substantially perpendicular to the axis of the shaft 40. In other embodiments, the through holes 41 may be formed in the shaft 40 at irregular angles or angles other than perpendicular to the axis of the shaft 40. In one embodiment, all of the components of the device 300 are formed from a medical grade skinned foam, such as an albuterol sulfate or other foamed material suitably robust to survive the harsh stomach 20 environment. Using a "skinned" foam traps air within the pores of the foam for flotation.

At least one of the first end 42 or the second end 44 comprises a concave dish 43, 45 having a larger radial dimension than the shaft 40 with the concave dish opening facing towards the midpoint of the shaft, thus creating something resembling mushroom-cap ends. The concave dishes 43, 45 may be integral to the shaft 40, such as by being molded therewith, or they may be coupled to the shaft 40 through any suitable means. In some embodiments, each dish 43, 45 comprises though holes 46 to allow the passage of sustenance or the contents 16 of the stomach 20. These through holes 46 may be regularly spaced or irregularly spaced, and may be a standard size or a varied size. As depicted, the through holes 46 are spaced at regular intervals and are one of two standard sizes.

Figure 3B:
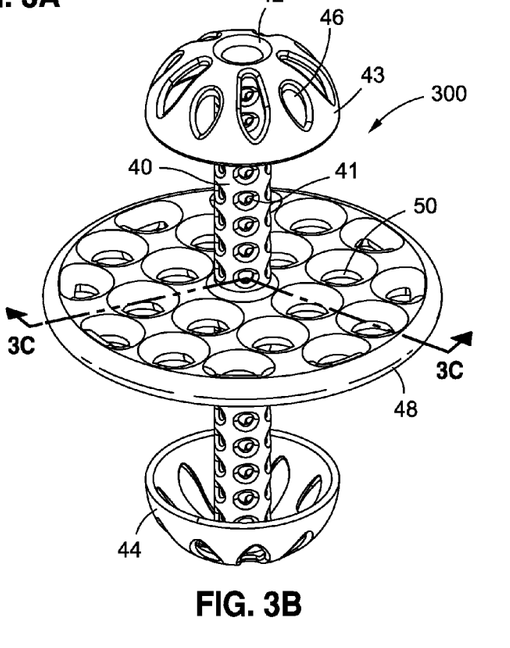
FIG. 3B illustrates a perspective view of the implantable foam cardia stimulation device of FIG. 3A in accordance with an embodiment of the present invention.
Figure 3C:
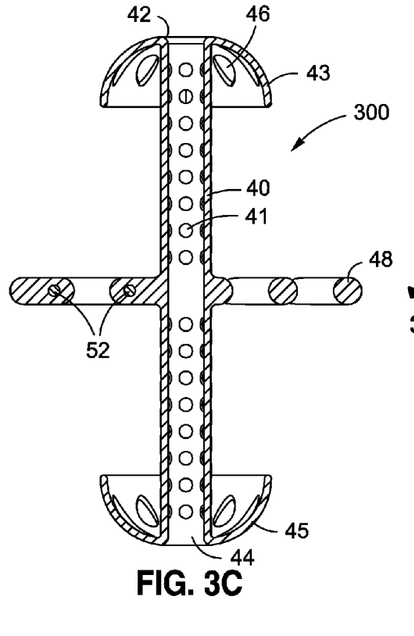
FIG. 3C illustrates a side cutaway view of the implantable foam cardia stimulation device of FIGS. 3A and 3B in accordance with an embodiment of the present invention.

Further, as depicted in FIGS. 3B and 3C, a central stabilizing disk 48 is coupled to and extends outward from the shaft 40 at approximately the midpoint of the shaft 40, though it could be located at any point along the shaft 40 in various embodiments. The disk 48 may be configured to aid the device 300 in floating, or to orient the device 300 in a preferred position, and preferably extends radially outward farther than the width of the end dishes 43, 45. In one embodiment, the disk 48 is integral to the shaft 40. The disk 48 may be oriented normal to the axis of the shaft. The disk 48 may be any suitable thickness and shape. In one embodiment, the disk 48 is substantially circular in shape and has a diameter approximately twice that of each of the end dishes 43, 45. In some embodiments, the disk 48 comprises axial openings 50 to allow the passage of sustenance or the contents 16 of the stomach 20 through the disk 48. These openings 50 may be regularly spaced or irregularly spaced, and may be a standard size or a varied size.

The central stabilizing disk 48 is desirably weighted axisymmetrically to provide stability to the device 300. Preferably, a plurality of weights 52 are embedded within the foam material of the disk 48. In one embodiment the weights 52 are metallic ball bearings. The weights 52 are distributed evenly around the axis of the device 300 so that they help stabilize the device in an upright orientation in the stomach. The stomach is generally oriented in the position shown in FIG. 3A when the person's torso is upright, and the device 300 is shown in an upright orientation. Due to the buoyancy of the device 300, and in particular the relatively wide central stabilizing disk 48, the device remains upright as it floats on the contents of the stomach. The embedded weights 52 assist in this stability.

Similar to the device 200, the device 300 is substantially symmetrical in the X, Y and/or Z axis. Thus, should the device 300 rotate or become inverted, the device 300 will function as intended. Stated another way, both the top and the bottom ends 42, 44 or external surfaces of the dishes 43, 45 are configured to stimulate an interior portion of the stomach 20, such as the cardia 14.

FIG. 3C depicts an embodiment of a cross-sectional view of the integral components of the device 300. The foam of the implantable foam cardia stimulation device 300 may be closed cell foam. In some embodiments, the foam of the device 300 may be a combination of closed cell foam and reticulated foam. In any event, a skin of less porous form of the same material is used to trap air within the pores of the foam for flotation. The materials selected for the device 300 components may be those that can survive the caustic environment of the stomach 20 and allow for convenient insertion into the stomach 20.

Since most of the device 300 is formed from a medical grade skinned foam, it may be substantially compressed in a first position for insertion in the stomach. Subsequent to transoral insertion into the stomach, such as being constrained through an access tube, the device 300 is permitted to expand into the illustrated embodiment. The device 300 may be subdivided into smaller pieces by a cutting tool, or the device 300 may be compressed and inserted back into a hollow cylinder for removal.

Figure 4A:
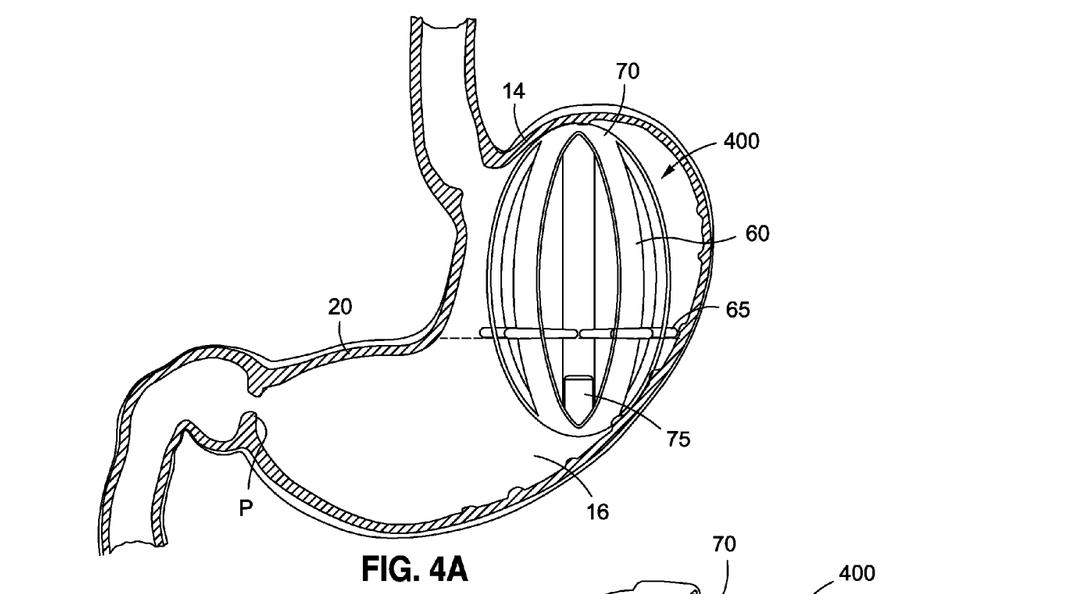
FIG. 4A illustrates a side view of an elevating implantable open frame buoyant cardia stimulation device post implantation in the stomach in accordance with an embodiment of the present invention.

FIG. 4A illustrates an implantable, open frame, buoyant foam cardia stimulation device 400 according to various embodiments. The device 400 may comprise a frame and frame struts 60 forming a generally prolate spheroid shape, which shape has been defined above and includes generally oval cross-sections oriented about a major central axis between end poles and defining a maximum diameter equator midway along the central axis. The frame struts 60 are spaced at a regular or irregular intervals or a combination thereof. Between each frame element 60 a circumferential opening leads to the open internal cavity of the device 400 circumscribed by the struts. The frame struts 60 may be made out of any suitable material, such as closed cell foam, reticulated foam or a combination thereof, and preferably define strips that are radially thin and relatively wide in the circumferential direction. The device 400 further comprises a stimulation surface 70 located proximate the intersection of the frame struts 60 at or near one end pole of the device 400.

Figure 4B:
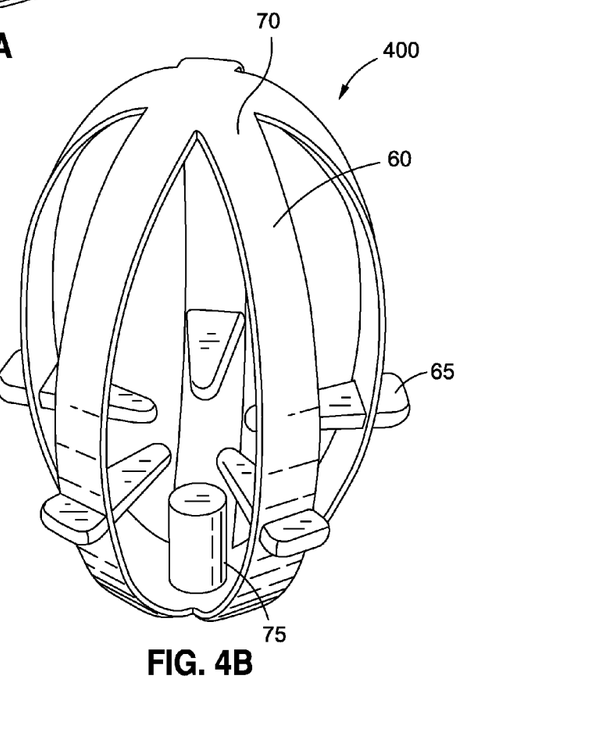
FIG. 4B illustrates a perspective view of the implantable open frame buoyant cardia stimulation device of FIG. 4A in accordance with an embodiment of the present invention.

Positioned along one or more of the frame struts 60 is a buoyant body 65. Though the buoyant body 65 may be fixed in place along the frame element 60 at any suitable location, in one embodiment, the buoyant bodies 65 are integral to the frame element and located on the struts in a plane perpendicular to the central axis ⅔ down from a top pole of the device 400. These buoyant bodies 65 may be made from any suitable material configured to aid in the buoyancy of the device, such as the same material as the frame element 60. The buoyant body 65 may be formed in any suitable shape. However, in one embodiment, the buoyant body 65 is wedge shaped. As shown in FIG. 4B, the wide portion of the wedge shaped buoyant body 65 extends out from the exterior surface of the frame element 60, and the narrow portion of the wedge shaped buoyant body 65 points inward towards the center cavity of the device from the interior surface of the frame element 60. This buoyant body 65 may be fixed at any suitable angle such as horizontal. The buoyant body 65 may be advantageously sized and oriented to aid the device 400 in floating on the contents 16 of the stomach 20. When floating, a greater portion of the device 400 may be higher above the surface of the contents 16 of the stomach 20 than a portion of the device 400 that is below the surface of the contents 16 of the stomach 20.

A weighted element 75 may be coupled to the device 400. This weighted element 75 may be any suitable element for providing mass. In one embodiment, the weighted element 75 comprises a steel cylinder encased in foam. The mass added may be selected based on being at least the minimum mass selectable to orient the device 400 in a position where the stimulation surface is capable of stimulating an interior surface of the stomach 20, such as the cardia 14.

The openings between the frame struts 60 and the internal open cavity of the open frame buoyant cardia stimulation device 400 may be configured to allow sustenance intake or the contents 16 of the stomach 20 to pass through the openings with relative ease. Further, the components of the device 400 may comprise through holes or surface features to allow the passage of sustenance intake or the contents 16 of the stomach 20.

Similar to the implantable foam cardia stimulation device 200 described above, the devices 300 or 400 may be at least partially compressed and inserted into a suitable implantation device, such as a hollow cylinder or Teflon tube, with the foam compressed to fit within the bounds of the cylinder. The hollow cylinder may be inserted into the mouth of the patient and fed down the esophagus towards the patient's stomach 20. Using tools, such as an endoscope or surgical grabber, the devices 300, 400 may be delivered from the hollow cylinder through the lower esophageal sphincter 22 into the stomach 20 of the patient. Once inserted into the stomach, the components of the devices 300, 400 may automatically return to their nominal, uncompressed state.

In various embodiments, and to facilitate removal, the devices 300 or 400 may be subdivided into smaller pieces by a cutting tool. In other embodiments, the devices 300 or 400 may be compressed and inserted back into a hollow cylinder for removal.

Similar to the implantable obesity treatment device 100, the devices 200, 300, and 400 may float on or near the surface of the contents 16 of the stomach 20. As the level of the surface of the contents 16 of the stomach 20 rises with sustenance intake, the stimulation surface 38 nears an interior surface of the stomach, such as the cardia 14, and applies a pressure. This pressure stimulates the release of satiety-inducing hormones, thus signaling the patient to slow or stop eating sooner than the patient would without the use of the devices 200, 300 or 400. Over time, this reduction in intake of sustenance contributes to weight loss of the patient.

In some embodiments, when at rest, or within a predetermined period between sustenance intake, the devices 100, 200, 300, 400, described herein are configured to not stimulate the cardia 14. The stimulation may occur after the surface level of the stomach 20 increases with sustenance intake.

The implantable devices described herein will be subjected to clinical testing in humans. The devices are intended to treat obesity, which is variously defined by different medical authorities. In general, the terms "overweight" and "obese" are labels for ranges of weight that are greater than what is generally considered healthy for a given height. The terms also identify ranges of weight that have been shown to increase the likelihood of certain diseases and other health problems. Applicants propose implanting the devices as described herein into a clinical survey group of obese patients in order to monitor weight loss.

The clinical studies will utilize the devices described above in conjunction with the following parameters.

Materials:
Silicone materials used include 3206 silicone for any shells, inflatable structures, or otherwise flexible hollow structures. Any fill valves will be made from 4850 silicone with 6% $BaSo_4$. Tubular structures or other flexible conduits will be made from silicone rubber as defined by the Food and Drug Administration (FDA) in the Code of Federal Regulations (CFR) Title 21 Section 177.2600.

Purposes:
the devices are for human implant,
the devices are intended to occupy gastric space while also applying intermittent pressure to various and continually changing areas of the stomach;
the devices are intended to stimulate feelings of satiety, thereby functioning as a treatment for obesity.

General implant procedures:
The device is intended to be implanted transorally via endoscope into the corpus of the stomach. However, other modes of access are contemplated, such as surgical/vascular access, various injection routes, percutaneous route, topical application, etc.
Implantation of the medical devices will occur via endoscopy.
Nasal/Respiratory administration of oxygen and isoflurane to be used during surgical procedures to maintain anesthesia as necessary.

One exemplary implant procedure is listed below.
a) Perform preliminary endoscopy on the patient to examine the GI tract and determine if there are any anatomical anomalies which may affect the procedure and/or outcome of the study.
b) Insert and introducer into the over-tube.
c) Insert a gastroscope through the introducer inlet until the flexible portion of the gastroscope is fully exited the distal end of the introducer.
d) Leading under endoscopic vision, gently navigate the gastroscope, followed by the introducer/over-tube, into the stomach.
e) Remove gastroscope and introducer while keeping the over-tube in place.
f) OPTIONAL: Place the insufflation cap on the over-tubes inlet, insert the gastroscope, and navigate back to the stomach cavity.
g) OPTIONAL: Insufflate the stomach with air/inert gas to provide greater endoscopic visual working volume.
h) Collapse the gastric implant and insert the lubricated implant into the over-tube, with inflation catheter following if required.
i) Under endoscopic vision, push the gastric implant down the over-tube with gastroscope until visual confirmation of deployment of the device into the stomach can be determined.
j) Remove the guide-wire from the inflation catheter is used.
k) If inflated: Inflate the implant using a standard BioEnterics Intragastric Balloon System ("BIB System") Fill kit.
l) Using 50-60 cc increments, inflate the volume to the desired fill volume.
m) Remove the inflation catheter via over-tube.
n) Inspect the gastric implant under endoscopic vision for valve leakage, and any other potential anomalies. Record all observations.
o) Remove the gastroscope from over-tube.
p) Remove the over-tube from the patient.

End Point Criteria:
Weight Loss
Comprehensive Metabolic Panel (CMP)
HbA1C
Lipid Panel
Tissue Samples/Response Unless otherwise indicated, all numbers expressing quantities of ingredients, properties, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references may have been made to patents and printed publications in this specification. Each of the above-cited references and printed publications are individually incorporated herein by reference in their entirety.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An implantable device configured to be placed in a stomach of a patient to elevate with increased stomach contents and stimulate the cardia of the stomach, the device comprising:
   an elastic elongated member that has a three-dimensional relaxed configuration and a generally linear stressed configuration, the relaxed configuration including a flotation portion commencing at a second end of the elongated member, the flotation portion having a generally two-dimensional shape defining a plane, the relaxed configuration further including a cardia-stimulating portion terminating at a first end of the elongated member, the cardia-stimulating portion being oriented generally perpendicular to the flotation portion;
   a plurality of discrete, spaced buoyant bodies individually affixed to the elongated member at spaced locations along the flotation portion, each of the buoyant bodies being hollow and sealed with a fixed amount of air or an inert gas trapped therein, each buoyant body being separately sealed from each other and from the elongated member, wherein the buoyant bodies provide buoyancy to the elongated member, and wherein each of the buoyant bodies having an inflated size that fits through the esophagus without the buoyant bodies being fully or partially deflated with respect the inflated size; and
   a stimulating body affixed to the first end of the elongated member, the stimulating body having a size adapted to fit through the esophagus without collapsing, wherein the device may be inserted transorally into the stomach in its stressed configuration and permitted to resume its three-dimensional relaxed configuration in the stomach with the cardia-stimulating portion extending toward the cardia region of the stomach, wherein the flotation portion floats on the surface of fluid within the stomach while the cardia-stimulating portion extends away from the surface of the fluid toward the cardia and wherein the buoyant bodies float on the surface of the fluid and the buoyant bodies are configured to support the elongated member on the surface of the contents of the stomach in an orientation where the stimulating body contacts the cardia as the fluid rises in the stomach.

2. The implantable device of claim 1, wherein the buoyant bodies are hollow and sealed so as to be non-inflatable.

3. The implantable device of claim 1, wherein the buoyant bodies are substantially spherical balloons.

4. The implantable device of claim 1, further comprising a weight located within the buoyant bodies comprising one of the group consisting of:
   a ball bearing, and
   a quantity of saline.

5. The implantable device of claim 1, wherein a plurality of buoyant bodies are evenly spaced around the flotation portion of the elongated member.

6. The implantable device of claim 1, wherein the flotation portion generally forms a ring, and the cardia-stimulating portion extends perpendicularly upward therefrom along a central axis of the ring.

7. The implantable device of claim 1, wherein the stimulating body is a three dimensional member having an outer surface defining a hollow interior.

8. The implantable device of claim 1, wherein a plurality of through holes are formed in the elongated member, wherein the through holes are sized to permit the passage of solids or liquids in the stomach through the elongated member and into and out of the holes.

9. An implantable device configured to be placed in a stomach of a patient to elevate with increased stomach contents and stimulate the cardia of the stomach, the device comprising:
   an elastic elongated member that has a three-dimensional relaxed configuration and a generally linear stressed configuration, the relaxed configuration including a flotation portion commencing at a second end of the elongated member, the flotation portion having a generally two-dimensional shape defining a plane, the relaxed configuration further including a cardia-stimulating portion terminating at a first end of the elongated member, the cardia-stimulating portion being oriented generally perpendicular to the flotation portion;
   a plurality of spaced buoyant bodies affixed to the elongated member at spaced locations along the flotation portion, the buoyant bodies being hollow and sealed with air or an inert gas trapped therein, wherein the buoyant bodies provide buoyancy to the elongated member, and
   wherein each of the buoyant bodies having an inflated size that fits through the esophagus without the buoyant bodies being fully or partially deflated with respect the inflated size; and
   a stimulating body affixed to the first end of the elongated member, the stimulating body having a size adapted to fit through the esophagus without collapsing, wherein the device may be inserted transorally into the stomach in its stressed configuration and permitted to resume its three-dimensional relaxed configuration in the stomach with the cardia-stimulating portion extending toward the cardia region of the stomach, wherein the flotation portion floats on the surface of fluid within the stomach while the cardia-stimulating portion extends away from the surface of the fluid toward the cardia and wherein the buoyant bodies float on the surface of the fluid and the buoyant bodies are configured to support the elongated member on the surface of the contents of the stomach in an orientation where the stimulating body contacts the cardia as the fluid rises in the stomach, wherein a plurality of through holes are formed in the elongated member, and the through holes are sized to permit the passage of solids or liquids in the stomach into and out of the holes.

* * * * *